(12) United States Patent
Honma et al.

(10) Patent No.: US 7,214,832 B2
(45) Date of Patent: May 8, 2007

(54) PROCESSES FOR THE PREPARATION OF BICYCLIC AMINOALCOHOLS

(75) Inventors: Tsunetoshi Honma, Osaka (JP); Yoshiharu Hiramatsu, Osaka (JP); Susumu Mitsumori, Osaka (JP)

(73) Assignee: Shionogi & Co., Ltd., Osaka (JP)

( * ) Notice: Subject to any disclaimer, the term of this patent is extended or adjusted under 35 U.S.C. 154(b) by 332 days.

(21) Appl. No.: 10/784,930

(22) Filed: Feb. 25, 2004

(65) Prior Publication Data
US 2004/0171882 A1 Sep. 2, 2004

Related U.S. Application Data

(62) Division of application No. 10/019,670, filed as application No. PCT/JP00/04171 on Jun. 26, 2000, now Pat. No. 6,723,857.

(30) Foreign Application Priority Data
Jul. 2, 1999 (JP) ................... 11-188674

(51) Int. Cl.
C07C 45/00 (2006.01)
(52) U.S. Cl. ...................... 568/348; 568/365
(58) Field of Classification Search ...................... None
See application file for complete search history.

(56) References Cited

U.S. PATENT DOCUMENTS

| | | | |
|---|---|---|---|
| 6,083,974 A | 7/2000 | Honma et al. | |
| 6,399,788 B1 | 6/2002 | Honma et al. | |

FOREIGN PATENT DOCUMENTS

| | | |
|---|---|---|
| JP | 6-239917 | 8/1994 |
| WO | 98/25919 | 6/1998 |
| WO | 99/50260 | 10/1999 |
| WO | 99/50261 | 10/1999 |
| WO | 99/62555 | 12/1999 |

OTHER PUBLICATIONS

Rerick et al, Tetrahedron Letters, Lithium Aluminum Hydride-Aluminum Chloride Reduction, 1963, pp. 629-634.*
Baciocchi, E., et al. "Synthesis of Unsymmetrical 1,4-Diketones by the Ceric Ammonium Nitrate Promoted Cross-Coupling of Trimethylsilyl Enol Ethers", Tetrahedron Letters, vol. 30, No. 28 (1989), pp. 3707-3710.
Baciocchi, E., et al. "Synthesis of 4-Oxoaldehydes by the Ceric Ammonium Nitrate Promoted Oxidative Addition of Trimethylsilyl Enol Ethers to Ethyl Vinyl Ether", Synlett, Nov. 1990, pp. 679-680.
Gregory, J.A., et al. "Synthesis of (endo) 3,9-Disubstituted Diazabicyclo[3.3.1]nonan-7-amines", Tetrahedron Letters, vol. 36, No. 1 (1995), pp. 155-158.
Baciocchi, E., et al. "Synthesis of 1,4-Dicarbonyl Compounds by the Ceric Ammonium Nitrate Promoted Reaction of Ketones With Vinyl and Isopropenyl Acetate", Tetrahedron Letters, vol. 28, No. 44 (1987), pp. 5357-5360.

Yoon, N.M., et al. "Selective Reductions. XII. Explorations in Some Representative Applications of Aluminum Hydride for Selective Reductions", Journal of American Chemical Society, vol. 90, No. 11 (1968), pp. 2927-2938.
Ragauskas, A.J., et al. "$^{13}$C magnetic resonance studies. 120. The Simmons-Smith reaction with some silyl enol ethers. Unusual ring expansions of some norcamphors", Can. J. Chem., vol. 63 (1985), pp. 2969-2974.
Patel, V., et al. "$^{13}$C magnetic resonance studies. 124. Preparative ring expansions of bicyclic ketones by homoketonization of cyclopropoxide analogs", Can. J. Chem, vol. 64 (1986), pp. 1440-1449.
Seno, K., et al. "Thromboxane $A_2$ Receptor Antagonists. III. Synthesis and Pharmacological Activity of 6,6-Dimethylbicyclo[3.1.1]heptane Derivatives with a Substituted Sulfonylamino Group at C-2", Chem. Pharm. Bull., vol. 37, No. 6 (1989), pp. 1524-1533.
Fluka Chemie AG: "Fluka Chemika-Biochemika", 1993, Fluka Chemie AG, Buchs/Switzerland, XP002242832, p. 545, No. 41661 and 41664 (DMPU).

(Continued)

Primary Examiner—Paul A. Zucker
(74) Attorney, Agent, or Firm—Wenderoth, Lind & Ponack, L.L.P.

(57) ABSTRACT

The present invention provides a process for the preparation of a bicyclic aminoalcohol which comprises reacting a starting compound, nopinone (I), with $XCH_2COOR^1$ wherein X is halogen, and $R^1$ is alkyl, in the presence of an additive and a base to produce a compound (II), converting it to oxime derivative (III), and reducing it with an aluminum hydride

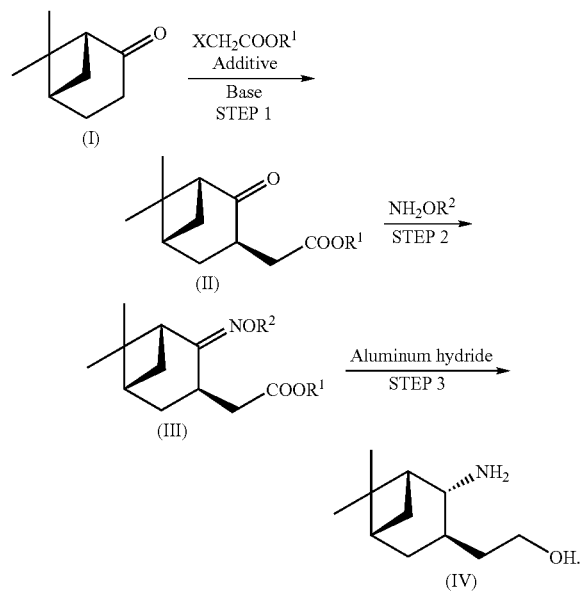

3 Claims, No Drawings

OTHER PUBLICATIONS

J. March, "Advanced Organic Chemistry, Reactions, Mechanisms, and Structure", 1985, John Wiley & Sons, New York, p. 1105.

D. Curran, et al., "Additions of Electrophilic Radicals to Electron Rich Alkenes by the Atom Transfer Method. Surmounting Potentially Reversible Radical Atom Transfer Reactions by Irreversible Ionic Reactions", *Tetrahedron Letters*, vol. 39, 1998, pp. 6629-6632.

* cited by examiner

PROCESSES FOR THE PREPARATION OF BICYCLIC AMINOALCOHOLS

This application is a Divisional application of Ser. No. 10/019,670, filed Jan. 2, 2002, now U.S. Pat. No. 6,723,857, which is a 371 application of PCT/JP00/04171, filed Jun. 26, 2000.

TECHNICAL FIELD

The present invention relates to processes for the preparation of bicyclic aminoalcohols.

BACKGROUND ART

The following scheme is disclosed in Chem. Pharm. Bull., 37(6), 1524–1533 (1989) as processes for the preparation of a bicyclic aminoalcohol (IV).

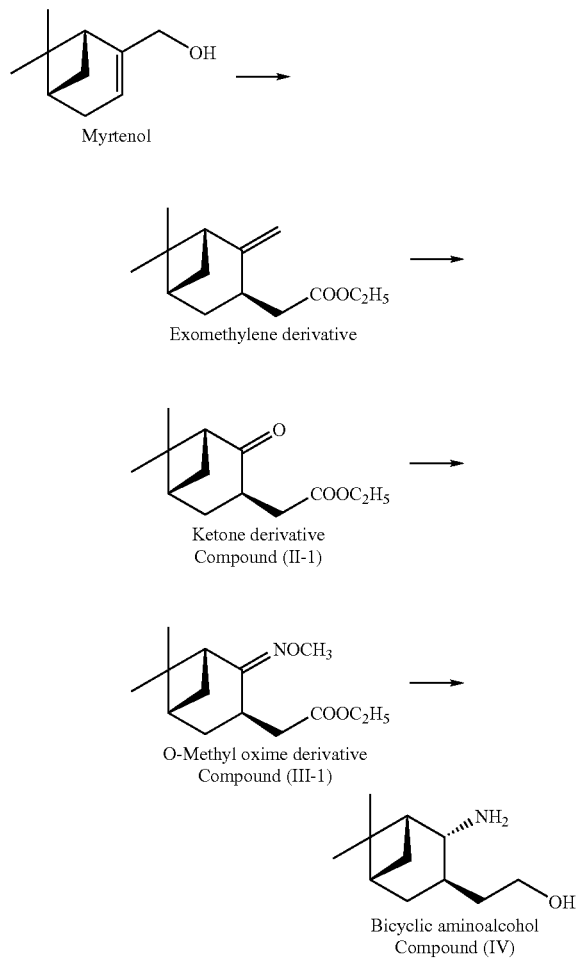

A starting material, myrtenol, is reacted with ethyl orthoformate to give an exomethylene derivative. The exomethylene derivative is oxidized by ozone to give a ketone derivative, compound (II-1), which is further reacted with O-methylhydroxyamine to give an O-methyloxime derivative, compound (III-1). The obtained O-methyloxime derivative is reduced in n-propanol with metallic sodium to give a bicyclic aminoalcohol, compound (IV).

It is disclosed in the above document that alkylation of nopinone, compound (I), gives a mixture of the starting material, a di-substituted product and a mono-substituted product as shown below. Moreover, the mono-substituted product is disclosed as a mixture of two stereo isomers.

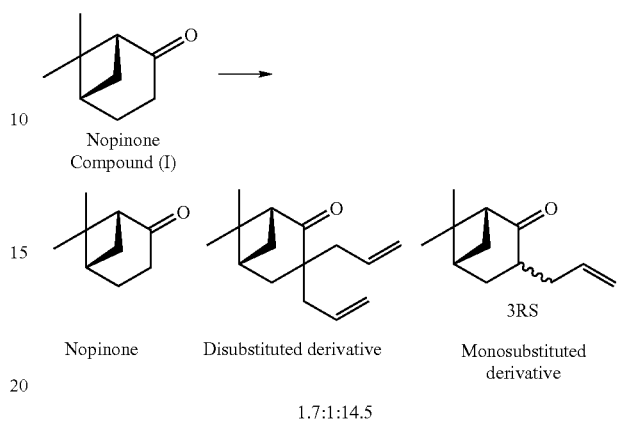

DISCLOSURE OF INVENTION

There are some problems in the above process for the preparation of the bicyclic aminoalcohol that the starting material, myrtenol, is expensive and not preferable in view of supply. Thus, another process for the preparation of the ketone derivative, compound (II-1), is desired. In the above method, the purity of the bicyclic aminoalcohol (compound (IV)) obtained through reduction of the O-methyloxime derivative (compound (III-1)) is not so high. When the bicyclic aminoalcohol is crystallized and purified as a salt with benzoic acid, the yield is only 39.6%.

A benzothiophene carboxamide derivative, compound (VIII):

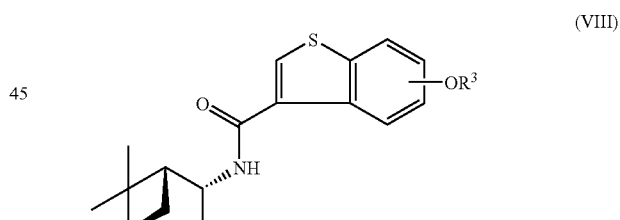

wherein $R^3$ is hydrogen, alkyl, acyl, alkylsulfonyl or arylsulfonyl, $R^4$ is hydrogen or alkyl, and a double bond represents E- or Z-configuration, is a high selective PGD2 receptor antagonist. WO 98/25919 discloses the following process for the preparation of the compound (VIII).

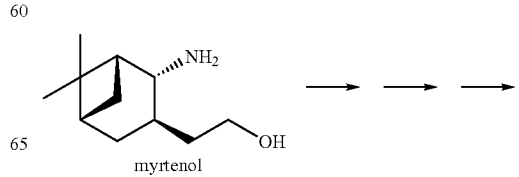

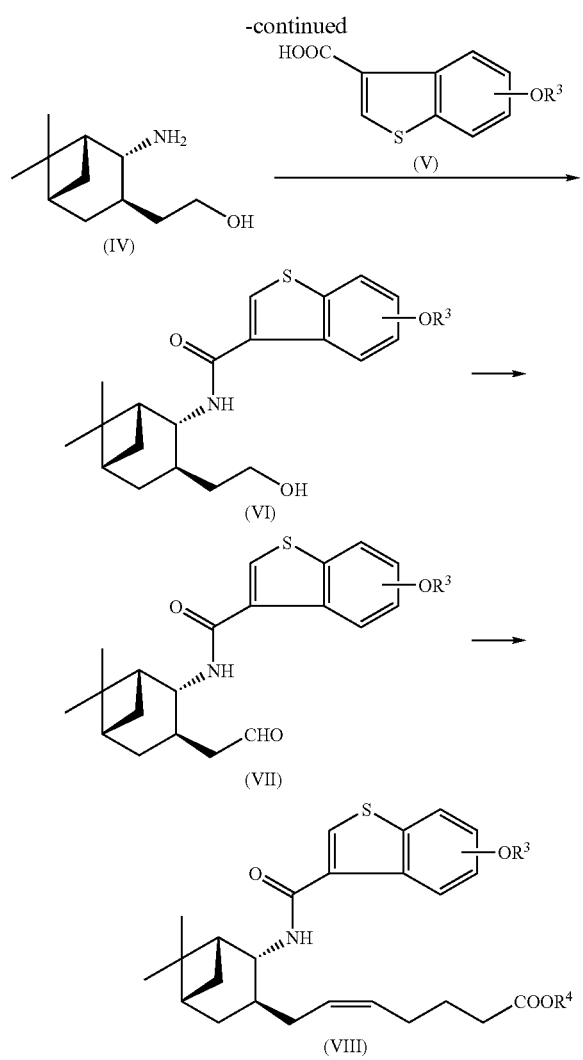

wherein $R^3$ is hydrogen, alkyl, acyl, alkylsulfonyl or arylsulfonyl, $R^4$ is hydrogen or alkyl, and a double bond represents E- or Z-configuration.

The bicyclic aminoalcohol of the formula (IV):

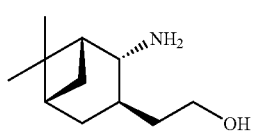
(IV)

is useful as an intermediate of the compound (VIII) and should be prepared at a low cost and stably provided.

But, a prior art of process for the preparation of the bicyclic aminoalcohol (IV) has the above problems.

On the other hand, as shown below, a method using an alkaline metal- or alkaline earth metal-substituted borohydride in the presence of a Lewis acid is known as a reduction of an O-methyloxime derivative (compound (III-1)) to a bicyclic aminoalcohol (compound (IV)).

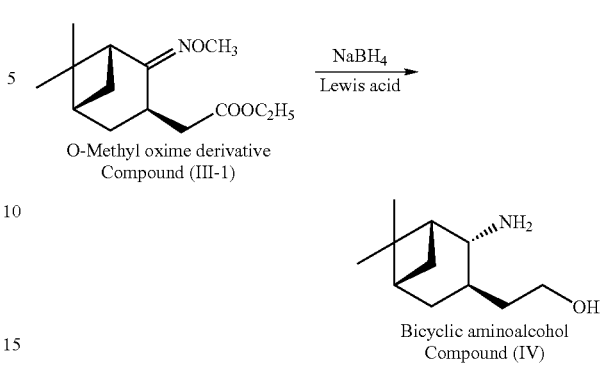

But the above method using such borohydrides is accompanied with production of diborane, so this method has a problem in view of safety for an industrial process.

The present inventors have found out a process for the preparation of the ketone derivative (compound (II)) from nopinone (compound (I)) and a novel process for the reduction of the O-methyloxime derivative or a more inexpensive oxime derivative (compound (III)) to the bicyclic aminoalcohol (compound (IV)), to develop a safe process for the preparation of the bicyclic aminoalcohol.

The present invention provides;

1) a process for the preparation of a compound (II):

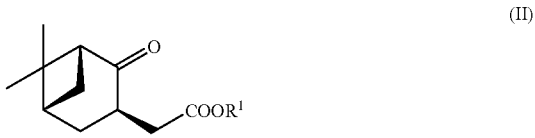
(II)

wherein $R^1$ is alkyl, which comprises reacting a compound (I):

(I)

with $XCH_2COOR^1$ wherein X is halogen, and $R^1$ is as defined above in the presence of an additive and a base, 2) a process for the preparation of a compound (IV):

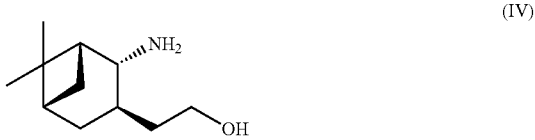
(IV)

which comprises reducing a compound (III):

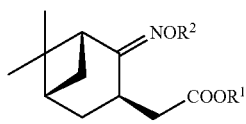
(III)

wherein R¹ is as defined above, and R² is hydrogen or alkyl, with an aluminum hydride,
3) a process for the preparation of a compound (IV):

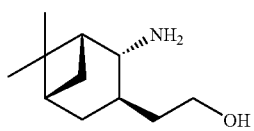
(IV)

which comprises reacting a compound (II):

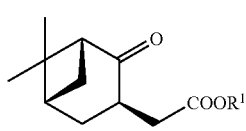
(II)

wherein R¹ is as defined above, with $NH_2OR^2$ wherein R² is as defined above to give a compound (III):

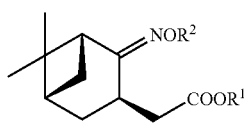
(III)

wherein R¹ and R² are as defined above, and reducing the compound (III) with an aluminum hydride,
4) a process for the preparation of a compound (III):

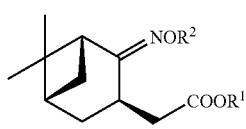
(III)

wherein R¹ and R² are as defined above, which comprises preparing a compound (II):

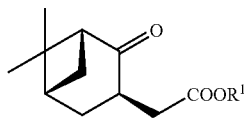
(II)

wherein R¹ is as defined above, through the process according to the above 1), and reacting the compound (II) with $NH_2OR^2$ wherein R² is as defined above, 5) a process for the preparation of a compound (IV):

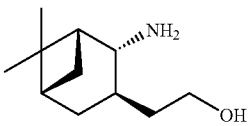
(IV)

which comprises preparing a compound (III):

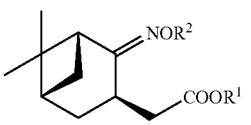
(III)

wherein R¹ and R² are as defined above through the process according to the above 4), and reducing the compound (III) with an aluminum hydride, 6) the process according to the above 2), 3) or 5) wherein the aluminum hydride is prepared by reacting a Lewis acid with lithium aluminum hydride or reacting concentrated sulfuric acid with lithium aluminum hydride, 7) a process for the preparation of a compound (IX):

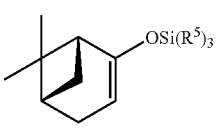
(IX)

wherein R⁵ each is independently alkyl, which comprises reacting a compound (I):

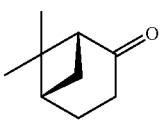
(I)

with $(R^5)_3SiX$ wherein R⁵ is as defined above, and X is halogen, in the presence of a base, 8) a process for the preparation of a compound (X):

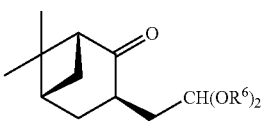
(X)

wherein R⁶ each is independently alkyl, which comprises reacting a compound (IX):

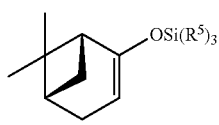

(IX)

wherein R⁵ each is independently alkyl, with CH₂=CHOR⁶ wherein R⁶ is as defined above in the presence of ceric ammonium nitrate (IV) in a solvent of R⁶OH wherein R⁶ is as defined above, 9) a process for the preparation of a compound (X):

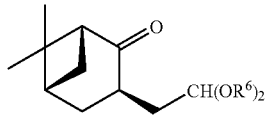

(X)

wherein R⁶ is as defined above, which comprises preparing a compound (IX):

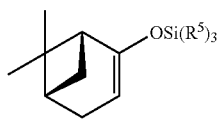

(IX)

wherein R⁵ is as defined above through the process according to the above 7), and reacting the compound (IX) with CH²=CHOR⁶ wherein R⁶ is as defined above in the presence of ceric ammonium nitrate (IV) in a solvent of R⁶OH wherein R⁶ is as defined above, 10) a process for the preparation of a compound (VI):

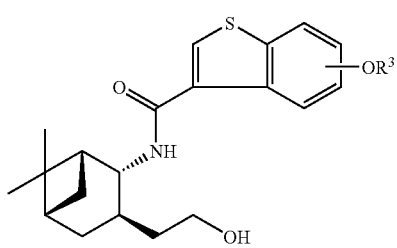

(VI)

wherein R³ is hydrogen, alkyl, acyl, alkylsulfonyl or arylsulfonyl, which comprises preparing a compound (IV):

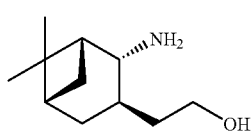

(IV)

through the process according to any one of the above 2), 3), 5) and 6), and reacting the compound (IV) or its salt with a compound (V):

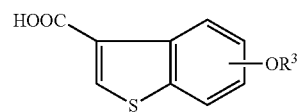

(V)

wherein R³ is as defined above or its reactive derivative, 11) a process for the preparation of a compound (VII):

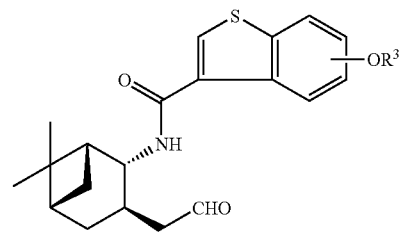

(VII)

wherein R³ is as defined above, which comprises preparing a compound (VI):

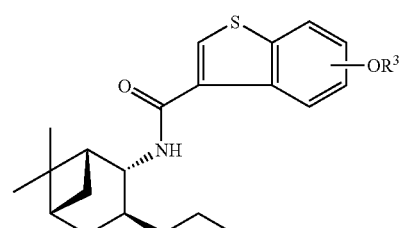

(VI)

wherein R³ is as defined above through the process according to the above 10), and oxidizing the compound (VI), 12) a process for the preparation of a compound (VII):

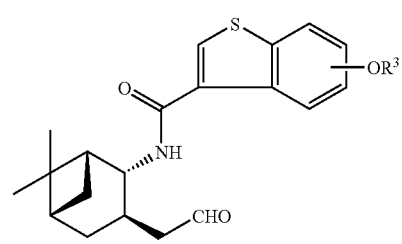

(VII)

wherein R³ is as defined above, which comprises preparing a compound (X):

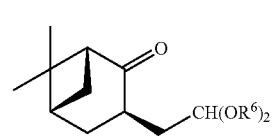

(X)

wherein $R^6$ is as defined above through the process according to the above 8) or 9), reacting the compound (X) with $NH_2OR^2$ wherein $R^2$ is as defined above to give a compound (XI):

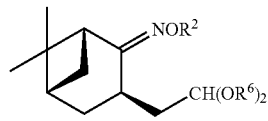
(XI)

wherein $R^2$ and $R^6$ are as defined above, reducing the compound (XI) to give a compound (XII):

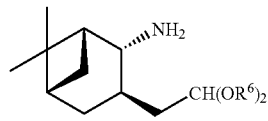
(XII)

wherein $R^6$ is as defined above, reacting the compound (XII) with a compound (V):

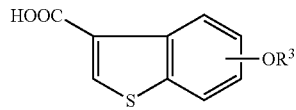
(V)

wherein $R^3$ is as defined above or its reactive derivative to give a compound (XIII):

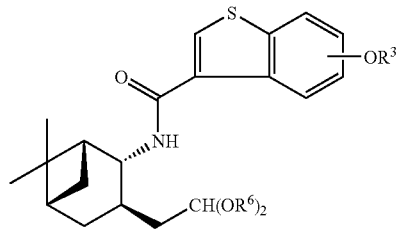
(XIII)

wherein $R^3$ and $R^6$ are as defined above, and reacting the compound (XIII) with an acid, 13) a process for the preparation of a compound (VIII):

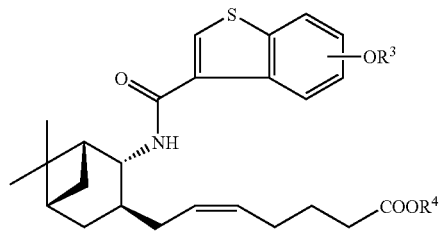
(VIII)

wherein $R^3$ is as defined above, $R^4$ is hydrogen or alkyl, and a double bond represents E- or Z-configuration, a pharmaceutically acceptable salt or hydrate thereof, which comprises preparing a compound (VII):

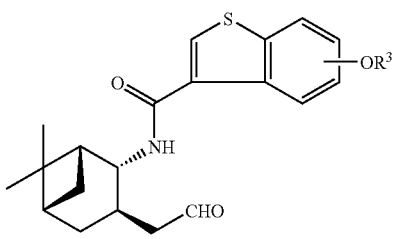
(VII)

wherein $R^3$ is as defined above through the process according to the above 11) or 12), reacting the compound (VII) with an ylide of the formula: $Ph_3P=CH(CH_2)_3COOR^4$ wherein $R^4$ is as defined above, and if desired, deprotecting.

The term "alkyl" includes straight or branched C1 to C6 alkyl, for example, methyl, ethyl, n-propyl, isopropyl, n-butyl, isobutyl, sec-butyl, tert-butyl, n-pentyl, isopentyl, neopentyl, tert-pentyl, n-hexyl, isohexyl or the like. Preferred is methyl or ethyl.

The term "acyl" includes carbonyl substituted with hydrogen or the above alkyl, for example, formyl, acetyl, propionyl, butyryl, isobutyryl, valeryl, isovaleryl, pivaloyl, hexanoyl or the like. Preferred is formyl or acetyl.

The term "alkylsulfonyl" includes sulfonyl substituted with the above alkyl, for example, methanesulfonyl, ethanesulfonyl or the like.

The term "arylsulfonyl" includes sulfonyl substituted with aryl. The term "aryl" includes a monocyclic aromatic carbocyclic group or polycyclic aromatic carbocyclic group, for example, phenyl, naphthyl or the like. Aryl may be substituted with the above alkyl. Examples of arylsulfonyl include benzenesulfonyl, p-toluenesulfonyl or the like.

The term "halogen" means fluoro, chloro, bromo or iodo.

BEST MODE FOR CARRYING OUT THE INVENTION

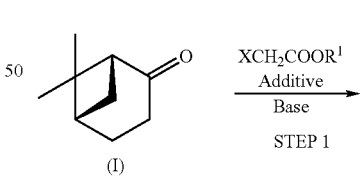
(I)

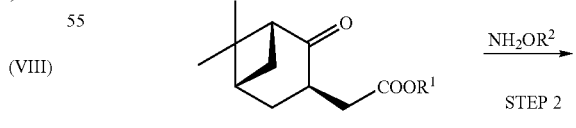
(II)

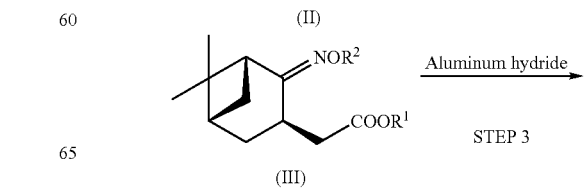
(III)

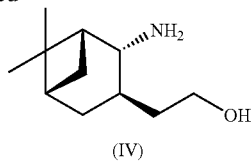

(IV)

wherein R¹ is alkyl, R² is hydrogen or alkyl, and X is halogen.

Step 1

This step shows a process for the preparation of a ketone derivative (compound (II)) from nopinone (compound (I)). A mono-substituted derivative (compound (II)) can be obtained in high yield by reacting a compound (I) with XCH₂COOR¹ wherein X and R¹ are defined above in the presence of an additive and a base, without producing a mixture of the starting material, a di-substituted derivative and a mono-substituted derivative as shown in the above document.

An additive includes a reagent controlling the stereochemistry, such as N,N,N',N'-tetramethylethylenediamine (TMEDA), hexamethylphosphoramide (HMPA), N,N'-dimethlpropyleneurea (DMPU), 1,3-dimethyl-2-imidazolidinone (DMI) or the like. Preferred is N,N'-dimethlpropyleneurea (DMPU) or 1,3-dimethyl-2-imidazolidinone (DMI). The amount of an additive is preferably 0.01 to 10.0 mole equivalent, more preferably 0.5 to 2.0 mole equivalent, and especially 1.0 to 1.5 mole equivalent to the compound (I).

A base includes a lithiation reagent such as lithium diisopropylamide (LDA), n-butyllithium or the like. Preferred is lithium diisopropylamide (LDA). A commercially available LDA may be used. LDA may be prepared by reacting diisopropylamine with n-butyllithium when it is used. The amount of a base is preferably 1.0 to 10.0 mole equivalent, more preferably 1.0 to 3.0 mole equivalent, and especially 1.0 to 1.5 mole equivalent to the compound (I).

XCH₂COOR¹ wherein X is halogen, and R¹ is alkyl, includes ethyl bromoacetate, methyl bromoacetate or the like. Preferred is ethyl bromoacetate. The amount of XCH₂COOR¹ wherein X and R¹ are as defined above is preferably 1.0 to 10.0 mole equivalent, more preferably 1.0 to 5.0 mole equivalent, and especially 2.0 to 3.0 mole equivalent to the compound (I).

The amount of XCH₂COOR¹ wherein X and R¹ are as defined above is preferably larger than that of a base. A preferred amount is: additive 1.0 mole equivalent, base 1.0 to 1.2 mole equivalent and XCH₂COOR¹ 2.0 to 3.0 mole equivalent to the compound (I).

It is preferred in this process that XCH₂COOR¹ is added to a mixture of the compound (I), an additive and a base. The compound (I), additive and base may be added in any order. For example, the addition can be performed in the order of compound (I), additive and base, or the order of base, additive and compound (I).

The reaction temperature is −100 to 100° C., preferably −70° C. to room temperature.

The reaction time is 0.5 to 50 hours, preferably 1 to 24 hours.

The reaction solvent includes an ether derivative (e.g., ethyl ether, tetrahydrofuran, 1,2-dimethoxyethane, dioxane, diethylene glycol dimethyl ether or the like), a hydrocarbon derivative (e.g., toluene, xylene) or a mixed solvent of an ether derivative and a hydrocarbon derivative.

Step 2

This process shows a process for the preparation of an oxime derivative (compound (III)) from a ketone derivative (compound (II)). A compound (III) can be prepared by reacting a compound (II) with NH₂OR² wherein R² is as defined above.

NH₂OR² wherein R² is as defined above includes hydroxylamine, O-methylhydroxylamine or the like.

The reaction temperature is 0 to 150° C., preferably 50 to 100° C. When NH₂OR² is hydroxylamine, the reaction is preferably carried out under 70° C. because the reaction at high temperature causes an isomerization.

The reaction time is 0.5 to 50 hours, preferably 1 to 24 hours.

Step 3

This step includes a process for the preparation of a bicyclic aminoalcohol (compound (IV)) from an oxime derivative (compound (III)). The bicyclic aminoalcohol (compound (IV)) can be prepared in high yield with high stereo selectivity and safety by reducing the oxime and ester parts of the oxime derivative (compound (III)) with an aluminum hydride at the same time.

An aluminum hydride can be prepared by reacting a Lewis acid or concentrated sulfuric acid with lithium aluminum hydride. The preparation can be carried out in the presence of a compound (III) or preferably before the addition of a compound (III).

A Lewis acid includes a halogenated compound such as halogenated tin, halogenated zinc, halogenated aluminum, halogenated titanium, halogenated boron, halogenated beryllium, halogenated zirconium, halogenated nickel or the like (e.g., stannous chloride, stannic chloride, aluminum chloride (AlCl₃), zinc chloride (ZnCl₂), beryllium chloride (BeCl₂), titanium tetrachloride, boron trifluoride, zirconium tetrachloride, nickel dichloride). Preferred is aluminum chloride, zinc chloride or beryllium chloride.

For example, an aluminum hydride (AlH₃) is produced in accordance with the following formulae.

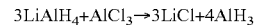

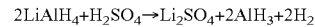

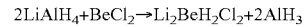

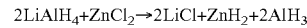

The reaction solvent includes ether derivatives (e.g., ethylether, tetrahydrofuran, 1,2-dimethoxyethane, dioxane, diethylene glycol dimethyl ether), hydrocarbon derivatives (e.g., toluene, xylene), a mixed solvent of ether derivatives and hydrocarbon derivatives. Preferred is tetrahydrofuran.

The amount of aluminum hydride is preferably 1.0 to 10.0 mole equivalent, more preferably 2.0 to 10.0 mole equivalent, and especially 2.0 to 5.0 mole equivalent to the compound (III).

In the preparation of aluminum hydride, the amount of a Lewis acid, which depends on the kind of Lewis acid, is preferably 0.25 to 2.5 mole equivalent, more preferably 0.5 to 2.5 mole equivalent, and especially 0.5 to 1.25 mole equivalent to the compound (III). In the above case, the amount of lithium aluminum hydride is preferably 0.75 to 7.5 mole equivalent, more preferably 1.5 to 3.75 mole equivalent to the compound (III).

When concentrated sulfuric acid is used for the preparation of aluminum hydride, the amount of concentrated sulfuric acid is preferably 0.5 to 5.0 mole equivalent, more preferably 1.0 to 5.0 mole equivalent, especially 1.0 to 2.5 mole equivalent to the compound (III). In the above case, the amount of lithium aluminum hydride is preferably 1.0 to 10.0 mole equivalent, more preferably 2.0 to 5.0 mole equivalent.

The amount of aluminum hydride is preferably 4.0 mole equivalent to the compound (III). Preferably, the amount of lithium aluminum hydride is 3.0 to 4.0 mole equivalent, and that of aluminum chloride or concentrated sulfuric acid is 1.0 to 2.0 mole equivalent.

The procedure is concretely explained below. Two or more mole equivalent of lithium aluminum hydride to the compound (III) is added to a solvent at 0° C. to room temperature. 0.33 to 0.5 mole equivalent of a Lewis acid or concentrated sulfuric acid is added thereto. In this case, the Lewis acid or concentrated sulfuric acid can be dissolved in the solvent in advance. To this suspension is added a starting material (an oxime derivative, compound (III)) dissolved in double or more volume of a solvent. The oxime derivative (compound (III)), lithium aluminum hydride, Lewis acid or concentrated sulfuric acid can be added in any order. Then, the reaction mixture is stirred at 0 to 150° C. for a few minutes to hours. The mixture is mixed with water, and a diluted mineral acid (e.g., diluted hydrochloric acid), then stirred for decomposing excess of lithium aluminum hydride or aluminum hydride. The reaction mixture may be poured into to the diluted mineral acid.

Then the mixture is neutralized with an alkali (e.g., sodium hydroxide), extracted with an organic solvent (e.g., ethyl acetate) and evaporated to give a bicyclic aminoalcohol (compound (IV)). If necessary, the purification of bicyclic aminoalcohol (compound (IV)) can be carried out by forming a crystalline salt with an appropriate acid (e.g., benzoic acid) and neutralizing with an alkali.

The desired compound, bicyclic aminoalcohol (compound (IV)) can be prepared in high yield with high stereo selectivity by the above method.

The process for the preparation of bicyclic aminoalcohol described above is novel and useful. As shown below, a combination of this process and the process for the preparation of the final target compound (compound (VIII)) contributes to safe and efficient production of compound (VIII).

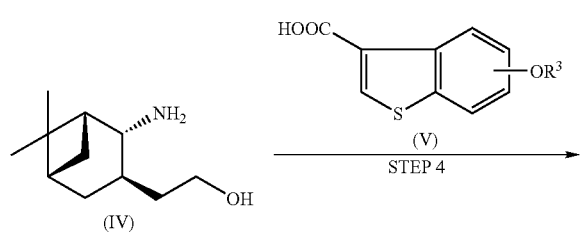

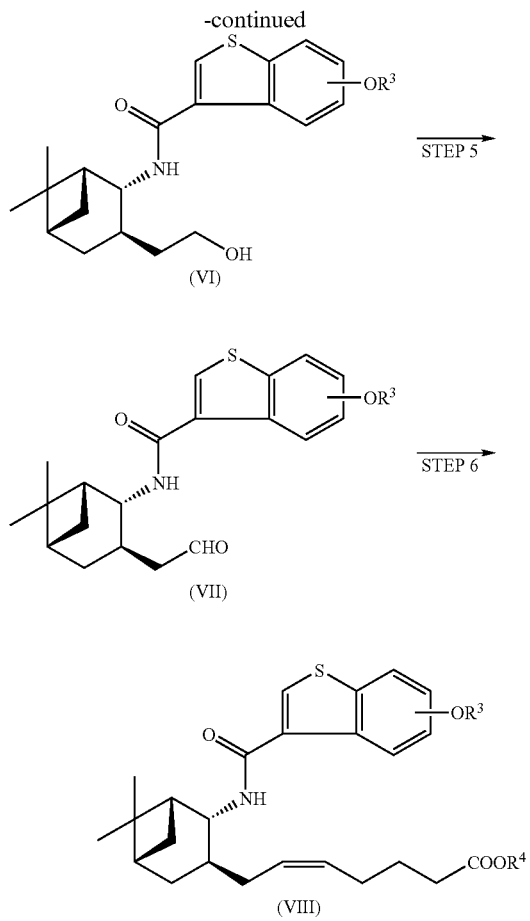

wherein $R^3$ is hydrogen, alkyl, acyl, alkylsulfonyl or arylsulfonyl, $R^4$ is hydrogen or alkyl, and a double bond represents E- or Z-configuration.

Step 4

This scheme shows a process for the preparation of an amide derivative (VI) which comprises acylating a bicyclic aminoalcohol (IV) or its salt with a carboxylic acid (V) or its reactive derivative.

The salt of bicyclic aminoalcohol (IV) includes a salt with an organic acid (e.g., benzoic acid) or an inorganic acid (e.g., hydrochloric acid, sulfuric acid).

The carboxylic acid (V) used in the acylation can be synthesized in accordance with a known method in literatures [for example, Nippon-Kagaku Zasshi vol. 88, No. 7, 758–763 (1967); Nippon-Kagaku Zasshi vol. 86, No. 10, 1067–1072 (1965); J. Chem. Soc. (C). 1899–1905(1967); J. Heterocycle. Chem. vol. 10, 679–681(1973)].

The term "reactive derivative" of carboxylic acid (V) refers to corresponding acid halides (e.g., chloride, bromide, iodide), acid anhydrides (e.g., mixed acid anhydride with formic acid or acetic acid), activated esters (e.g., succinimide ester), and the like, and includes acylating agents generally used for the acylation of amino group. For example, to obtain acid halides, a carboxylic acid is reacted with thionyl halide (e.g., thionyl chloride), phosphorous halide (e.g., phosphorous trichloride, phosphorous pentachloride), oxalyl halide (e.g., oxalyl chloride), or the like, according to a known method (e.g., Shin-jikken Kagaku Koza, vol. 14, p.

1787 (1978); Synthesis 852–854(1986); Shin-jikken Kagaku Koza vol. 22, p. 115 (1992)).

The acylation can be carried out under ordinary conditions used for the acylation of amino group. For example, when a carboxylic acid halide is used, the reaction is carried out according to a method commonly known as "Schotten-Baumann reaction". In general, carboxylic acid halide is added dropwise to an aqueous alkaline solution of amine with stirring and under cooling while removing the generating acid with alkali. Alternatively, when a carboxylic acid is used as a free acid not a reactive derivative, the reaction can be conducted conventionally in the presence of a coupling agent generally used in the coupling reaction between an amine and a carboxylic acid, such as dicyclohexylcarbodiimide (DCC), 1-ethyl-3-(3-dimethylaminopropyl)-carbodiimide or N,N'-carbonyldiimidazole.

Step 5

This step is related to the oxidation of an alcohol (VI) to an aldehyde (VII). Such a reaction can be conducted by using an oxidizing agent of chromium oxide type such as Jones reagent, Collins reagent or pyridinium chlorochromate. Further, oxidation with manganese dioxide or Swern oxidation with dimethyl sulfoxide are also applicable.

The other oxidation can be carried out with an oxidizing agent(s) such as halo oxoacid in the presence of TEMPO. Examples of TEMPO include 2,2,6,6-tetramethyl-piperidine-1-oxyl, 4-methoxy-2,2,6,6-tetramethylpiperidine-1-oxyl, 4-acetylamino-2,2,6,6-tetramethylpiperidine-1-oxyl, 4-benzoyloxy-2,2,6,6-tetramethylpiperidine-1-oxyl, and 4-cyano-2,2,6,6-tetramethylpiperidine-1-oxyl. Examples of halo oxoacid include sodium hypochlorite, sodium hypobromite, sodium bromite and higher bleaching powder.

Step 6

This step is related to the formation of a double bond by reacting an aldehyde (compound (VII)) with an ylide (Ph$^3$P=CH(CH$_2$)$_3$COOR$^4$ wherein R$^4$ is hydrogen or alkyl).

The reaction forming a double bond can be carried out in a conventional manner for Wittig reaction. The ylides used in the reaction can be synthesized, in the presence of a base, from a phosphonium salt which has been synthesized from triphenylphosphine and an alkyl halide having a desired alkyl group to be condensed, for example, 5-bromopentanoic acid. Preferred is Ph$_3$P=CH(CH$_2$)$_3$COOH.

Examples of a base include dimsyl sodium, dimsyl potassium, sodium hydride, n-butyl lithium, potassium t-butoxide and lithium diisopropylamide. The reaction is accomplished within several hours at room temperature in a solvent such as ether, tetrahydrofuran, n-hexane, 1,2-dimethoxyethane or dimethyl sulfoxide.

The double bond of the alkenylene side chain (5-heptenylene chain) on a compound (VIII) may be in the E- or Z-configuration.

A compound wherein R$^3$ is hydrogen can be prepared by deprotecting R$^3$ under an acidic condition (e.g., hydrochloric acid, sulfuric acid, boron tribromide), a neutral condition (e.g., trimethylsilyl iodide) or a basic condition (e.g., sodium hydroxide, potassium hydroxide, barium hydroxide). The reaction is accomplished within several tens minutes to several hours with heating in a solvent such as methanol-water, ethanol-water, acetone-water, acetonitrile-water, or the like, preferably dimethyl sulfoxide-water. The OR$^3$ may be positioned at any of 4-, 5-, 6- and 7-positions and preferably at 5-position.

The compound (VIII) prepared from the above processes can be formed into a salt. Examples of the salt include alkali metal salts such as lithium salt, sodium salt or potassium salt and the like, alkali earth metal salts such as calcium salt and the like, ammonium salt, salts with an organic base such as tromethamine, trimethylamine, triethylamine, 2-aminobutane, tert-butylamine, diisopropylethylamine, n-butylmethylamine, n-butyldimethylamine, tri-n-butylamine, cyclohexylamine, dicyclohexylamine, N-isopropylcyclohexylamine, furfurylamine, benzylamine, methylbenzylamine, dibenzylamine, N,N-dimethylbenzylamine, 2-chlorobenzylamine, 4-methoxybenzylamine, 1-naphthalenemethylamine, diphenylbenzylamine, triphenylamine, 1-naphthylamine, 1-aminoanthracene, 2-aminoanthracene, dehydroabiethylamine, N-methylmorpholine or pyridine, or amino acid salts such as lysine salt or arginine salt.

A hydrate of a compound (VIII) or its salt includes monohydrate, dihydrate, monohydrate of sodium salt, monohydrate of half calcium salt, dihydrate of half calcium salt or the like.

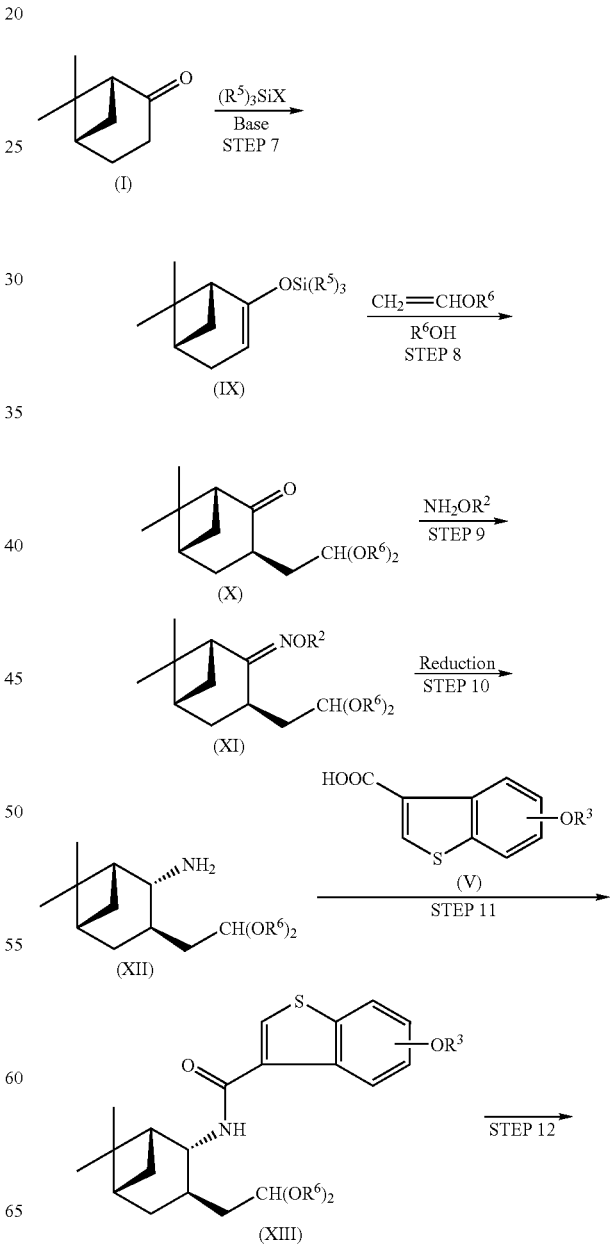

-continued

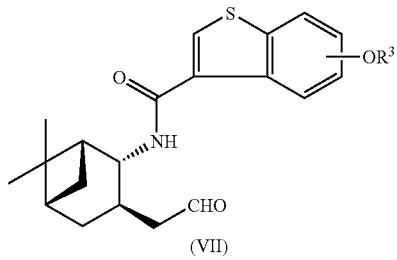

(VII)

wherein $R^2$ is hydrogen or alkyl, $R^5$ each is independently alkyl, $R^6$ is alkyl, $R^3$ is hydrogen, alkyl, acyl, alkylsulfonyl or arylsulfonyl, and X is halogen.

Step 7

This step is related to the preparation of a silyl ether (compound (IX)) by reacting nopinone (compound (I)) with a compound of the formula: $(R^5)_3SiX$ wherein $R^5$ each is independently alkyl, and X is halogen, in the presence of a base.

A base includes a lithiation agent such as lithium diisopropylamide, lithium bis(trimethylsilyl)amide. The amount of a base is 1.0 to 2.0 mole equivalent, especially 1.0 to 1.5 mole equivalent to the compound (I).

A compound of the formula: $(R^5)_3SiX$ includes chlorotrimethylsilane, bromotrimethylsilane, chlorotriethylsilane or the like. The amount of a compound of the formula: $(R^5)_3SiX$ is 1.0 to 2.0 mole equivalent, especially 1.0 to 1.5 mole equivalent to the compound (I).

The present reaction is accomplished within several hours to several tens hours under −100° C. to 100° C., especially −70° C. to room temperature.

In the present step, a compound (I), a base and a compound of the formula: $(R^5)_3SiX$ can be added in any order. Preferably, a base is added under cooling to compound (I), and the mixture is stirred for several minutes to several hours, followed by adding a compound of the formula: $(R^5)_3SiX$. After the addition of a base, the mixture can be warmed up to approximately 0° C., cooled, and mixed with a compound of the formula: $(R^5)_3SiX$.

The reaction solvent includes a non-polar solvent such as tetrahydrofuran, dioxane, diethyl ether or the like.

Step 8

This step is related to the preparation of a compound (X) by reacting a silylether derivative (compound (IX)) with a compound of the formula: $CH_2=CHOR^6$ wherein $R^6$ is alkyl, in the presence of ceric ammonium nitrate (IV) in a solvent of $R^6OH$ wherein $R^6$ is as defined above.

A compound of the formula: $CH_2=CHOR^6$ includes methyl vinyl ether ($R^6$ is methyl), ethyl vinyl ether ($R^6$ is ethyl), n-propyl vinyl ether ($R^6$ is n-propyl), n-butyl vinyl ether ($R^6$ is n-butyl), vinyl acetate ($R^6$ is acetyl) or the like. The amount of a compound of the formula: $CH_2=CHOR^6$ is 1.0 to 30.0 mole equivalent, especially 10.0 to 20.0 mole equivalent to the compound (IX).

$R^6OH$ includes an alchol having $R^6$ corresponding to $R^6$ of a compound of the formula: $CH_2=CHOR^6$ used in the present step. When a compound of the formula: $CH^2=CHOR^6$ is methyl vinyl ether, ethyl vinyl ether, n-propyl vinyl ether and n-butyl vinyl ether, $R^6OH$ is methanol, ethanol, n-propanol and n-butanol, respectively.

The amount of ceric ammonium nitrate (IV) is 1.0 to 5.0 mole equivalent, especially 1.0 to 2.0 mole equivalent to the compound (IX).

Preferably, this step is performed in the presence of a base. Examples of a base include calcium carbonate, sodium carbonate, sodium hydrogen carbonate or the like. The amount of a base is 1.0 to 5.0 mole equivalent, especially 1.0 to 3.0 mole equivalent to the compound (IX).

The present reaction is accomplished within several hours to several tens hours under −100° C. to 100° C., especially 0° C. to room temperature.

In the present step, a compound (IX), a base, ceric ammonium nitrate (IV), $R^6OH$ and a compound of the formula: $CH_2=CHOR^6$ can be added in any order. Preferably, a compound (IX) and a compound of the formula: $CH^2=CHOR^6$ are added under cooling to a solution of a base and ceric ammonium nitrate (IV) in a solvate of $R^6OH$.

Step 9

This step is related to the preparation of an oxime derivative (compound (XI)) by reacting a ketone derivative (compound (X)) with $NH_2OR^2$ wherein $R^2$ is as defined above. This step can similarly be performed in accordance with Step 2.

Step 10

This step is related to the preparation of a compound (XII) by reducing an oxime derivative (compound (XI)) with a reducing agent.

The present reduction should be carried out under a condition not influencing the group of the formula: —CH$(OR_6)_2$ of the compound (XI). Preferred is a reduction under a basic condition, for example, reduction with sodium metal in alchol.

The reaction temperature is −100° C. to 100° C., especially −50° C. to 50° C.

Step 11

This step is related to the preparation of a compound (XIII) by reacting a compound (XII) with a carboxylic acid (V) or its reactive derivative. The present step can similarly be performed in accordance with Step 4.

Step 12

This step is related to the preparation of an aldehyde derivative (compound (VII)) by hydrolyzing a group of the formula: —CH$(OR^6)_2$ of the compound (XIII).

This hydrolysis can be carried out preferably under an acidic condition at −100° C. to 100° C., specially 0° C. to room temperature. The reaction time is several minutes to several tens hours.

The compound (VII) prepared in this step is identical to a compound (VII) prepared in Step 5. A compound (VIII) can be prepared through Step 6 by using the compound (VII).

The following Examples are provided to further illustrate the present invention in more detail and should not be interpreted in any way as to limit the scope thereof. The abbreviations used in the Examples have the following meanings:

Ph: phenyl;
Ac: acetyl;
TMEDA: N,N,N',N'-tetramethylethylenediamine;
HMPA: hexamethylphosphoramide;
DMPU: N,N'-dimethylpropyleneurea;
DMI: 1,3-dimethyl-2-imidazolidinone;
CAN: ceric ammonium nitrate(IV).

EXAMPLE

Reference Example 1

Preparation of (1R)-(+)-nopinone (2)

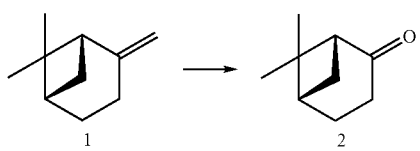

(1R)-(+)-Nopinone (2) was prepared in accordance with the method described in J. Grimshaw, J. T. Grimshaw, and G. R. Juneja, J. Chem. Soc., Perkin Trans. 1 1972, 50.

Example 1

Preparation of [(1R,3R,5S)-2-oxo-10-norpinan-3-yl]acetic acid ethyl ester (3)

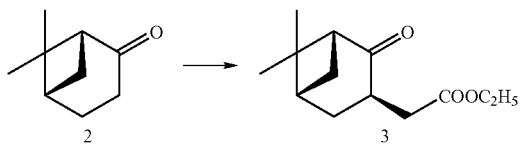

To a solution of diisopropylamine (12.2 ml, 0.087 mol) in tetrahydrofuran (60 ml) was added dropwise under −60° C. a 1.57 M solution of n-butyllithium in hexane (55.3 ml, 0.0868 mol). After stirring at the same temperature for 30 minutes, 1,3-dimethyl-2-imidazolidinone (DMI) (8.0 ml, 0.0732 mol) was added dropwise thereto. To the mixture was added dropwise under −60° C. a solution of (R)-(+)-nopinone (10.0 g, 0.0724 mol) in tetrahydrofuran (10 ml). The mixture was warmed to 0° C. by removing the ice bath, stirred under ice cooling for 30 minutes, cooled at −70° C., and mixed under −60° C. with ethyl bromoacetate (24.0 ml, 0.216 mol). The mixture was warmed to 0° C. by removing the ice bath and stirred under ice cooling for 2 hours. To the reaction mixture were added a saturated aqueous solution of ammonium chloride (10 ml) and ice water (150 ml) and twice extracted with toluene (100 ml). The toluene layer was twice washed with 0.5 mol dm$^{-3}$ hydrochloric acid (100 ml) and water (50 ml) and dried over anhydrous magnesium sulfate. The solvent and excess of ethyl bromoacetate were removed under reduced pressure to give 19.4 g of the titled compound (3) as yellow oil. Yield: 119% (Crude). The compound was used without purification.

$^1$H-NMR (CDCl$_3$, 300 MHz) δ 0.95 and 1.34 (each 3H, each s), 1.27 (3H, t, J=7.01 Hz), 1.40 (1H, d, J=9.9 Hz), 1.67 (1H, m), 2.25 (1H, m), 2.33–2.42 (2H, m), 2.56–2.65 (2H, m), 4.14–4.21 (2H, m).

Example 2 to 5

Preparation of [(1R,3R,5S)-2-oxo-10-norpinan-3-yl]acetic acid ethyl ester (3)

[(1R,3R,5S)-2-Oxo-10-norpinan-3-yl]acetic acid ethyl ester (3) was prepared by using the following additives (TMEDA, HMPA, DMPU) in place of 1,3-dimethyl-2-imidazolidinone (DMI) in Example 1. The results are shown in Table 1. Ref. No. 1 shows the case with no additive.

TABLE 1

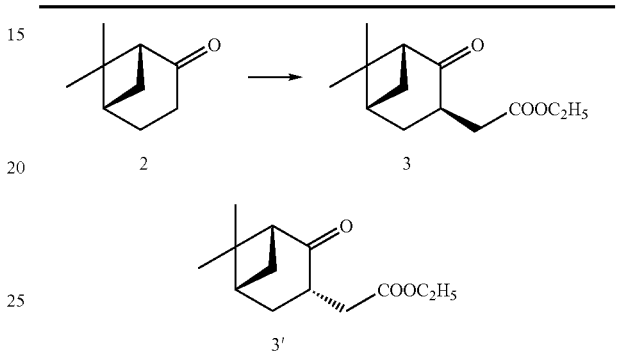

Preparations of [(1R, 3R, 5S)-2-oxo-10-norpinan-3-yl] acetic acid ethyl ester (3) by using an additive

| Example | LDA (eq) | Solvent | Additive | BrCH$_2$COOC$_2$H$_5$ (eq) | (3 + 3'):2 | Ratio of 3 | 3' |
|---|---|---|---|---|---|---|---|
| Ref No.1 | 1.2 | THF | none | 3 | 4.6:1 | 76 | 24 |
| Ex. No.2 | 1.2 | THF | TMEDA | 3 | 5.5:1 | 89 | 11 |
| Ex. No.3 | 1.2 | THF | HMPA | 3 | 7.8:1 | 98 | 2 |
| Ex. No.4 | 1.2 | THF | DMPU | 3 | 20:1 | 97 | 3 |
| Ex. No.5 | 1.2 | THF | DMPU | 1.5 | 25:1 | 82 | 18 |

Example 6

Preparation of [(1R,3R,5S)-2-hydroxyimino-10-norpinan-3-yl]acetic acid ethyl ester (4a)

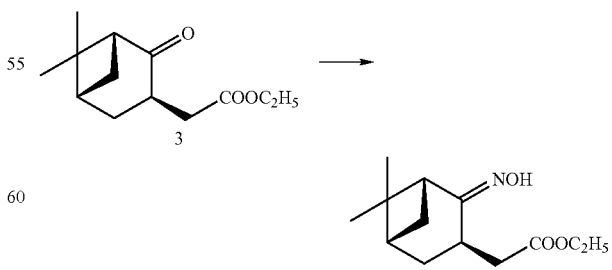

To a solution of compound (3) (5.00 g, 0.0223 mol) in ethanol (22.5 ml) were added hydroxylamine hydrochloride (2.48 g, 0.0357 mol) and pyridine (2.82 g, 0.0357 mol). The mixture was stirred at 60° C. for 2.5 hours. The reaction mixture was concentrated under reduced pressure, diluted with water, acidified with hydrochloric acid, and extracted with ethyl acetate. The organic layer was washed with water and 1% aqueous solution of sodium hydrogen carbonate, and dried over anhydrous magnesium sulfate. The solvent was removed under reduced pressure to give 5.37 g of the titled compound (4a) as colorless oil. Yield: 100%.

$[\alpha]_D^{24}$ +55.3° (c=1.01%, CH$_3$OH)

Example 7

Preparation of [(1R,3R,5S)-2-methoxyimino-10-norpinan-3-yl]acetic acid ethyl ester (4b)

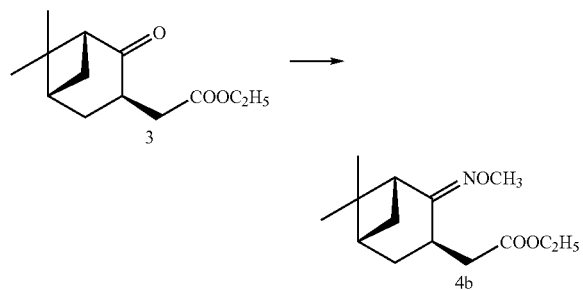

To a solution of a compound (3) prepared in the above step (19.4 g, 0.0724 mol) in ethanol (80 ml) were added O-methylhydroxylammonium chloride (7.86 g, 0.0941 mol) and pyridine (7.44 g, 0.0941 mol) and mixture was refluxed for 3 hours with stirring. The reaction mixture was concentrated under reduced pressure, diluted with water (50 ml) and 1 mol dm$^{-3}$ hydrochloric acid (25 ml) and twice extracted with toluene (100 ml). The toluene layer was washed with water (50 ml) and 1% aqueous solution of sodium hydrogen carbonate (50 ml), dried over anhydrous magnesium sulfate. The solvent was removed under reduced pressure to give 18.12 g of the titled compound (4b) as yellow oil. Yield: 98.8% (Crude).

IR(Film): 1738, 1630 cm$^{-1}$. $[\alpha]_D^{24}$ +69.5° (c=1.00%, CH$_3$OH)

Example 8

Preparation of [(1R,2R,3R,5S)-2-amino-10-norpinan-3-yl]ethanol benzoic acid salt (5)

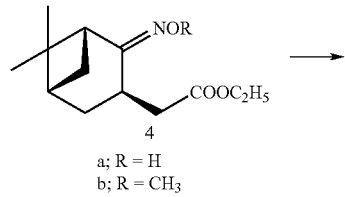

a; R = H
b; R = CH$_3$

-continued

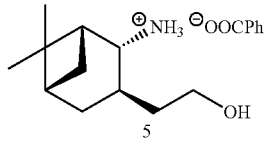

Example 8-1

Preparation from Compound (4a) (Part 1)

To a suspension of lithium aluminum hydride (455 mg, 0.012 mol) in tetrahydrofuran (8 ml) was added under ice cooling aluminum chloride (533 mg, 0.004 mol) and the mixture was stirred at room temperature for 30 minutes. A solution of compound (4a) (960 mg, 0.004 mol) in tetrahydrofuran (2.5 ml) was added thereto dropwise under ice cooling. The mixture was stirred at room temperature for 30 minutes and refluxed for 3 hours. To the reaction mixture was gradually added dropwise under ice cooling methanol (4 ml) and water (2 ml) and refluxed with stirring for 30 minutes. Insoluble substance was filtered and washed with methanol. The washing solvent was mixed with the filtrate and concentrated under reduced pressure. To the residue was added 10% brine (5 ml) and 1 mol dm$^{-3}$ solution of sodium hydroxide (1.5 ml). The mixture was twice extracted with ethyl acetate (15 ml). The organic layer was washed with 10% brine (5 ml), dried over anhydrous magnesium sulfate and evaporated under reduced pressure to give 694 mg of the residue as colorless oil. The residue was dissolved in diethylether (10 ml) and a solution of benzoic acid (462 mg, 0.00379 mol) in diethyl ether (5 ml) was added thereto and stirred. The precipitated crystal was filtered and washed with diethyl ether to give 968 mg of benzoic acid salt of aminoalcohol (5) as colorless crystal. Mp. 177–183° C. Yield: 79.2%.

$[\alpha]_D^{25}$ +24.8° (c=1.00%, CH$_3$OH) Elemental Analysis for C$_{18}$H$_{27}$NO$_3$ Calculated (%): C, 70.79; H, 8.91; N, 4.59. Found (%): C, 70.63; H, 8.81; N, 4.60.

Example 8-2

Preparation from Compound (4a). (Part 2)

To a suspension of lithium aluminum hydride (607 mg, 0.016 mol) in tetrahydrofuran (10 ml) was added dropwise concentraed sulfuric acid (0.42 ml, 0.008 mol) under ice cooling with stirring. The mixture was stirred at room temperature for 1 hour. A solution of compound (4a) (963 mg, 0.004 mol) in tetrahydrofuran (2.5 ml) was added thereto dropwise under ice cooling, and the mixture was stirred at room temperature for 30 minutes and refluxed for 2 hours. To the reaction mixture was gradually added dropwise under ice cooling methanol (4 ml), and followed by adding water (2 ml). The mixture was refluxed for 30 minutes. Insoluble substance was filtered and washed with methanol. The washing solvent was mixed with the filtered solvent and concentrated under reduced pressure. To the residue were added 10% brine (5 ml) and 1 mol dm$^{-3}$ aqueous solution of sodium hydroxide (1.5 ml). The mixture was twice extracted with ethyl acetate (15 ml). The organic layer was washed with 10% brine (5 ml), dried over anhydrous magnesium sulfate and evaporated under reduced pressure to give 681 mg of the residue as colorless oil. The residue was dissolved in diethyl ether (10 ml), mixed with a solution of benzoic acid (454 mg, 0.00372 mol) in diethyl ether (5 ml) and stirred. The precipitated crystal was filtered and washed with diethyl ether to give 953 mg of benzoic acid salt of aminoalcohol (5) as colorless crystal. Mp. 173–182° C. Yield: 78.0%.

$[\alpha]_D^{25}$+25.1° (c=1.01%, $CH_3OH$) Elemental Analysis for $C_{18}H_{27}NO_3$ Calculated (%): C, 70.79; H, 8.91; N, 4.59. Found (%): C, 70.56; H, 8.68; N, 4.60.

Example 8-3

Preparation from Compound (4a). (Part 1)

To a suspension of lithium aluminum hydride (4.07 g, 0.107 mol) in tetrahydrofuran (60 ml) was added under ice cooling aluminum chloride (4.77 g, 0.0358 mol). The mixture was stirred at room temperature for 30 minutes. A solution of compound (4a) (9.06 g, 0.0358 mol) in tetrahydrofuran (60 ml) was added thereto dropwise under ice cooling, and the mixture was stirred at room temperature for 30 minutes and refluxed for 2 hours. To the reaction mixture was gradually added dropwise under ice cooling methanol (60 ml), and followed by adding water (30 ml). The mixture was refluxed for 30 minutes. Insoluble substance was filtered and washed with methanol. The washing solvent was mixed with the filtrate and concentrated under reduced pressure. To the residue were added 10% brine (15 ml) and 4 mol $dm^{-3}$ aqueous solution of sodium hydroxide (2.6 ml). The mixture was twice extracted with ethyl acetate (50 ml). The organic layer was washed with 10% brine (15 ml), dried over anhydrous magnesium sulfate and evaporated under reduced pressure to give 6.09 g of the residue as colorless oil. The residue was dissolved in diethylether (50 ml), mixed with a solution of benzoic acid (4.05 g, 0.0332 mol) in diethylether (30 ml) and stirred. The precipitated crystal was filtered and washed with diethylether to give 8.80 g of benzoic acid salt of aminoalcohol (5) as colorless crystal. Yield: 80.5%.

IR(KBr): 3420, 2600, 1621, 1523, 1386 $cm^{-1}$. $^1$H-NMR ($CDCl_3$, 300 MHz) δ 0.72 (1H, d, J=9.9 Hz), 1.06 and 1.13 (each 3H, each s), 1.40 (1H, m), 1.56–1.92 (3H, m), 2.12–2.36 (4H, m), 3.29 (1H, m), 3.62 (1H, m), 3.78 (1H, m), 7.32–7.47 (3H, m), 7.97–8.04 (2H, m). $[\alpha]_D^{25}$+23.7° (c=1.00%, $CH_3OH$) Elemental Analysis for $C_{18}H_{27}NO_3$ Calculated (%): C, 70.79; H, 8.91; N, 4.59. Found (%): C, 70.57; H, 8.86; N, 4.62.

Example 8-4

Preparation from Compound (4a). (Part 2)

To a suspension of lithium aluminum hydride (455 mg, 0.012 mol) in tetrahydrofuran (8 ml) was added dropwise under ice cooling with stirring concentrated sulfuric acid (0.32 ml, 0.006 mol). The mixture was stirred at room temperature for 1 hour. A solution of compound (4b) (1.013 g, 0.004 mol) in tetrahydrofuran (2.5 ml) was added dropwise under ice cooling, stirred at room temperature for 30 minutes and refluxed for 2 hours. To the reaction mixture was gradually added dropwise under ice cooling methanol (4 ml), mixed with water (2 ml) and refluxed for 30 minutes. Insoluble substance was filtered and washed with methanol. The washing solvent was mixed with the filtrate and concentrated under reduced pressure. To the residue were added 10% brine (5 ml) and 1 mol $dm^{-3}$ aqueous solution of sodium hydroxide (1.5 ml). The mixture was twice extracted with ethyl acetate (15 ml). The organic layer was washed with 10% brine (5 ml), dried over anhydrous magnesium sulfate and evaporated under reduced pressure to give 690 mg of the residue as colorless oil. The residue was dissolved in diethyl ether (10 ml), mixed with a solution of benzoic acid (460 mg, 0.00376 mol) in diethyl ether (5 ml) and stirred. The precipitated crystal was filtered and washed with diethyl ether to give 976 mg of benzoic acid salt of aminoalcohol (5) as colorless crystal. Mp. 175–184° C. Yield: 79.9%.

$[\alpha]_D^{25}$+25.3° (c=1.01%, $CH_3OH$) Elemental Analysis for $C_{18}H_{27}NO_3$ Calculated (%): C, 70.79; H, 8.91; N, 4.59. Found (%): C, 70.68; H, 8.86; N, 4.61.

Example 9

Preparation of (1R,2R,3R,5S)-2-[(5-benzenesulfonyloxybenzo[b]thiophen-3-ylcarbonylamino)-10-norpinan-3-yl]ethanol (6)

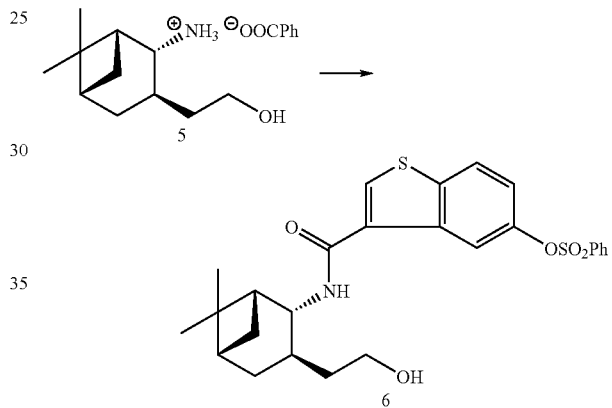

(+)-2-[(1R,2R,3R,5S)-2-Amino-10-norpinan-3-yl]ethanol benzoic acid salt (5) (5.1 g, 16.7 mmol) prepared in Example 8 was suspended in water (10 ml). To the suspension was added 1 mol $dm^{-3}$ HCl (17 ml) and the deposited benzoic acid was removed by extracting with ethyl acetate. The organic layer was washed with water (10 ml). To the combined aqueous layer was added 4 mol $dm^{-3}$ sodium hydroxide (9.2 ml, 36.8 mmol) under ice-cooling, and a solution of 5-benzenesulfonyloxybenzo[b]thiophene-3-carbonyl chloride (5.89 g, 16.7 mmol) in tetrahydrofuran (36 ml) was then added dropwise over 15 minutes with stirring. After stirring for another 1 hour at the same temperature, 1 mol $dm^{-3}$ hydrochloric acid (4 ml) was added and extracted with ethyl acetate. The organic layer was washed with water, dried over anhydrous magnesium sulfate and then the solvent was distilled under reduced pressure to provide 8.00 g (95.6%) of the title compound (6) as colorless amorphous.

$^1$H NMR ($CDCl_3$, 300 MHz) δ 0.96 (1H, d, J=9.9 Hz), 1.12 and 1.26 (each 3H, each s), 1.50–2.42 (9H, m), 3.69–3.82 (2H, m), 4.30 (1H, m), 6.21 (1H), d, J=8.1 Hz), 7.06 (1H, dd, J=2.4 and 8.7 Hz), 7.51–7.56 (2H, m), 7.67 (1H, m), 7.73 (1H, d, J=8.7 Hz), 7.85–7.88 (2H, m), 7.88 (1H, s), 8.06 (1H, d, J=2.4 Hz)

$[\alpha]_D^{25}$+35.7° (c=1.00%, $CH_3OH$)

Example 10

Preparation of (1R,2R,3R,5S)-3-formylmethyl-2-[(5-benzenesulfonyloxybenzo[b]thiophen-3-ylcarbonylamino)-10-norpinan-3-yl] (7) (Part 1)

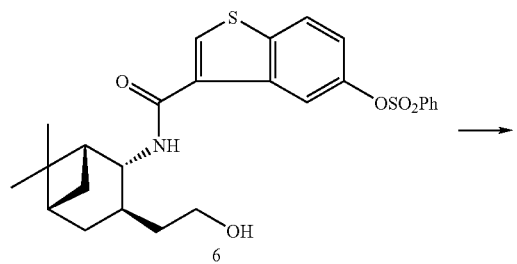

The compound (6) (9.72 g, 18.3 mmol) was dissolved in ethyl acetate (70 ml). To the solution were added TEMPO (2,2,6,6-tetramethylpiperidine-1-oxyl, 14.3 mg, 0.005 equivalent) and potassium bromide (218 mg, 0.1 equivalent). 0.41 mol dm$^{-3}$ Aqueous sodium hypochlorite (45 ml of a solution adjusted to pH 9.5 with sodium hydrogen carbonate, 1 mole equivalent) was added dropwise over 3 minutes with stirring while maintaining the inner temperature at −1° C.–6° C. After 10 minutes at this temperature, the two layers were separated and the aqueous layer was extracted with ethyl acetate. The organic layer was washed with water, dried over anhydrous magnesium sulfate and then the solvent was distilled under reduced pressure to provide 9.10 g (100%) of the title compound (7) as colorless amorphous.

IR (CHCl$_3$); 3443, 3093, 3066, 3030, 3016, 2925, 2871, 2828, 2729, 1720, 1655, 1599, 1558, 1513, 1377 cm$^{-1}$ $^1$H NMR (CDCl$_3$, 300 MHz) δ 0.97(1H, d, J=10.2 Hz), 1.17 and 1.28 (each 3H, each s), 1.46 (1H, m), 2.03 (1H, m), 2.22 (1H, m), 2.36–2.60 (3H, m), 2.69 (1H, ddd, J=1.2, 8.7 and 17.4 Hz), 3.14 (1H, dd, J=4.5 and 17.4 Hz), 4.28 (1H, m), 6.18 (1H, d, J=8.1 Hz), 7.09 (1H, dd, J=2.4 and 8.7 Hz), 7.50–7.55 (2H, m), 7.67 (1H, m), 7.75 (1H, d, J=8.7 Hz), 7.85–7.89 (2H, m), 7.89 (1H, s), 8.03 (1H, d, J=2.4 Hz), 9.80 (1H, d, J=1.2 Hz) [α]$_D^{23}$+31.8° (c=1.00%, CH$_3$OH)

Example 11

Preparation of (1R,2R,3R,5S)-3-formylmethyl-2-[(5-benzenesulfonyloxybenzo[b]thiophen-3-ylcarbonylamino)-10-norpinan-3-yl] (7) (Part 2)

To a solution of dimethyl sulfoxide (3.16 ml, 44.5 mmol) in dimethoxyethane (50 ml) was added at −60° C. to −65° C. oxalyl chloride (1.91 ml, 21.9 mmol). A solution of alchol (6) (7.352 g, 14.7 mmol) in 1,2-dimethoxyethane (58 ml) was added dropwise thereto at the same temperature. The mixture was stirred at −55° C. to −60° C. for 30 minutes, mixed with triethylamine (6.1 ml), stirred for 30 minutes and warmed up to room temperature by removing ice bath. The reaction mixture was diluted with water (100 ml) and extracted with toluene. The organic layer was washed with water, dried over anhydrous magnesium sulfate and evaporated under reduced pressure. The obtained residue was chromatographed on silica gel (hexane:ethyl acetate=5:5 to 4:6) to give 7.32 g of the titled compound (7) described above as colorless amorphousness. Yield: 100%.

Example 12

Preparation of (5Z)-7-[(1R,2R,3S,5S)-2-(5-benzenesulfonyloxybenzo[b]thiophen-3-ylcarbonylamino)-10-norpinan-3-yl]-5-heptenoic acid (8)

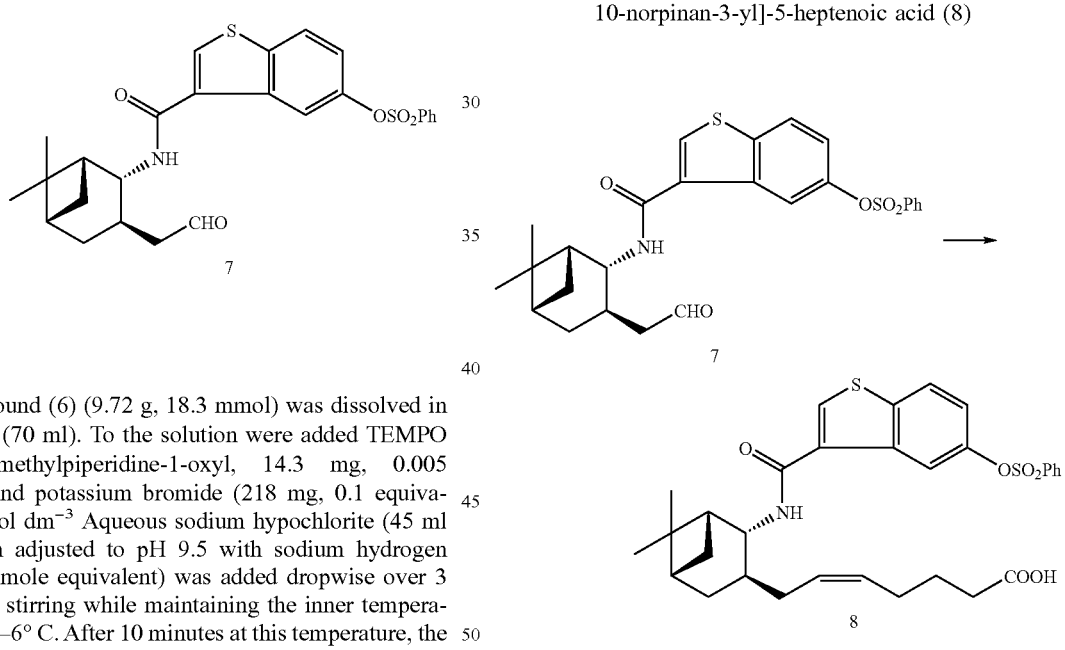

4-Carboxybutyltriphenylphosphonium bromide (12.17 g, 27.5 mmol) and potassium t-butoxide (7.19 g, 64.1 mmol) were suspended in tetrahydrofuran (64 ml) and the mixture was stirred under ice-cooling for 1 hour. To the reaction mixture was added a solution of compound (7) (9.11 g, 18.3 mmol) in tetrahydrofuran (27 ml) over 15 minutes, and stirring was continued for 2 hours at the same temperature. The reaction mixture was diluted with water (80 ml) and washed with toluene (2×10$^5$ ml). After the aqueous layer was adjusted to pH 8.1 with 5 N hydrochloric acid (4.8 ml), anhydrous calcium chloride (8.1 g, 73 mmol) dissolved in water (16 ml) was added and the mixture was extracted with ethyl acetate (2×100 ml). To the organic layer was added water (100 ml) and the aqueous layer was adjusted to pH 2 with 5 N hydrochloric acid and extracted with ethyl acetate. The organic layer was washed with water, dried over anhydrous magnesium sulfate and then the solvent was distilled off under reduced pressure to provide 11.06 g of the compound (8), which was used without purification.

Example 13

Preparation of (5Z)-7-[(1R,2R,3S,5S)-2-(5-hydroxy-benzo[b]thiophen-3-ylcarbonylamino)-10-norpinan-3-yl]-5-heptenoic acid (9)

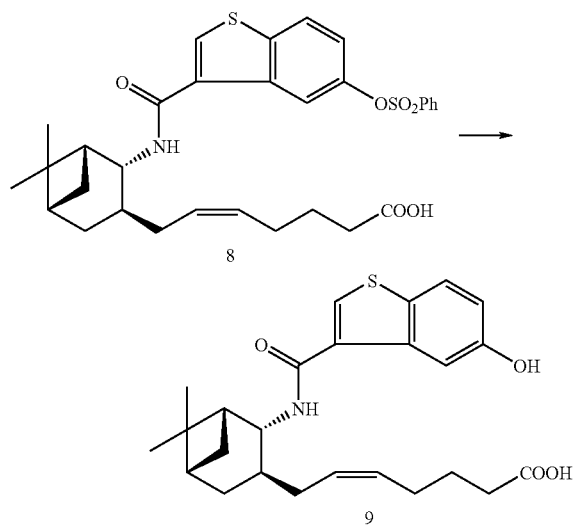

The compound (8) (11.06 g, 18.3 mmol) prepared in above (3) was dissolved in dimethyl sulfoxide (22 ml). To the solution was added 4 N sodium hydroxide (27.5 ml), and the mixture was heated at 55° C. for 2 hours with stirring. The reaction mixture was diluted with water (130 ml) and washed with toluene (2×65 ml). The aqueous layer was acidified with 5 N hydrochloric acid and then extracted with ethyl acetate. The organic layer was washed with water, dried over anhydrous magnesium sulfate and then the solvent was distilled under reduced pressure to provide 8.26 g of the crude desired compound (9). The product was dissolved in methanol (40 ml) and water (16 ml), and the mixture was seeded and gradually cooled with stirring. The deposited crystals were filtered and washed with water:methanol (2:5) to provide 6.35 g of the desired compound (9). Yield: 78.6%. The crystals were dissolved in methanol (40 ml), and water (12 ml) was added with stirring over 7 minutes. After adding seeds, the solution was continuously stirred at 25° C. for 1 hour. Additional water (7 ml) was added over 40 minutes and stirring was continued for 1.5 hours at 25° C. The deposited crystals were filtered and washed with water: methanol (3:5) (8 ml) to provide 6.14 g of the almost colorless desired compound (9). Yield: 76.0%, mp 145–146° C.

IR (Nujol); 3313, 3096, 3059, 3001, 1717, 1627, 1603, 1548, 1469, 1440 cm$^{-1}$ $^1$H NMR (CDCl$_3$, 300 MHz) δ 1.02 (1H, d, J=10.2 Hz), 1.12 and 1.24 (each 3H, each s), 1.56–2.55 (14H, m), 4.29 (1H, m), 5.32–5.51 (2H, m), 6.20 (1H, d, J=9.3 Hz), 7.01 (1H, dd, J=2.4 and 9.0 Hz), 7.66 (1H, d, J=9.0 Hz), 7.69 (1H, s), 8.03 (1H, d, J=2.4 Hz) [α]$_D^{24}$=50.7°(c=1.01,CH$_3$OH) Elemental Analysis for C$_{25}$H$_{31}$NO$_4$S Calculated (%): C, 68.00; H, 7.08; N, 3.17; S, 7.26; Found (%): C, 67.84; H, 7.08; N, 3.24; S, 7.31;

Example 14

Preparation of (1R)-nopinonetrimethylsilylenolether (10)

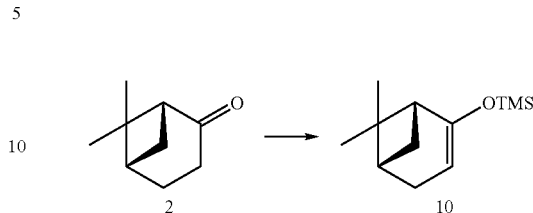

To a solution of 1.0 g (7.24 mmol) of (1R)-(+)-nopinone (2) in 10 ml of tetrahydrofuran under nitrogen atmosphere was gradually added at −78° C. 5.4 ml (10.8 mmol) of 2M solution of lithium diisopropylamide in tetrahydrofuran. After 10 minutes, the mixture was warmed to 0° C. and stirred for 30 minutes. Then, the reaction mixture was cooled to −78° C. 2.8 ml (22.1 mmol) of chlorotrimethylsilane was added thereto and stirred for 1 hour. The mixture was mixed at −78° C. with saturated sodium hydrogen carbonate and warmed to room temperature. The water layer was extracted three times with hexane. The combined organic layer was washed with saturated aqueous solution of ammonium chloride and saturated brine, dried over anhydrous magnesium sulfate and evaporated under reduced pressure. The obtained residue was chromatographed on silica gel (hexane:ethylacetate=9:1) to give 1.25 g of the titled compound (10) as pale yellow oil. Yield: 82%.

$^1$H-NMR (CDCl$_3$, 300 MHz) δ 0.19 (9H, s), 0.93 (3H, s), 1.28 (3H, s), 1.30 (1H, m), 1.96–2.25 (4H, m), 2.39 (1H, dt, J=8.4 and 5.7 Hz), 4.56 (1H, m). IR(CHCl$_3$): 1605, 1247 cm$^{-1}$. [α]$_D^{25}$−15.1±0.6°(c=1.00, CHCl$_3$)

Example 15

Preparation of [(1R,3R,5S)-2-oxo-10-norpinan-3-yl]acetaldehyde diethyl acetal

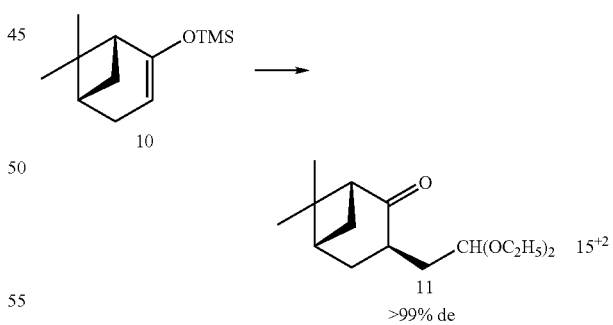

To 2.0 ml of ethyl alcohol were added under nitrogen atmosphere 0.357 g (3.57 mmol) of calcium carbonate and 1.30 g (2.37 mmol) of ceric ammonium nitrate (IV). To the solution was added dropwise for 5 minutes under ice cooling a solution of 0.25 g (1.19 mmol) of compound (10) in 2.30 ml (23.76 mmol) of ethyl vinyl ether. After stirring for 3 hours, the solution was warmed to room temperature. After 15 hours, the solution was filtered through the celite, mixed with water, and extracted three times with ethyl acetate. The combined organic layer was washed with saturated brine, dried over anhydrous magnesium sulfate, evaporated under reduced pressure. The obtained crystal was chromatographed on silica gel (hexane:ethylacetate=9:1) to give 0.1415 g of the titled compound (11) as pale yellow oil. (11:2=68:32)

$^1$H-NMR(CDCl$_3$, 300 MHz) δ 0.90 (3H, s), 1.21 (3H, t, J=7.2 Hz), 1.22 (3H, t, J=7.2 Hz), 1.35–1.82 (3H, m), 2.22–2.35 (4H, m), 2.46–2.61 (4H, m), 3.47–3.74 (5H, m), 4.71 (1H, t, J=6.3 Hz). IR(CHCl$_3$): 2929, 1699, 1473, 1456, 1444, 1389, 1373, 1346, 1317, 1296, 1198, 1061, 1016 cm$^{-1}$. $[\alpha]_D^{25}$+31.2±0.7°(c=1.00, CHCl$_3$) Elemental Analysis for C$_{15}$H$_{26}$O$_3$ 0.1H$_2$O Calculated (%): C, 70.33; H, 10.31. Found (%): C, 70.46; H, 10.21.

INDUSTRIAL APPLICABILITY

The present invention provides a process for the safe, efficient, and low cost preparation of a bicyclic aminoalcohol (compound (IV)) from nopinone (compound (I)), resulting in inexpensive production of a PGD$_2$ receptor antagonist, compound (VIII).

What is claimed is:
1. A process for the preparation of a compound (II):

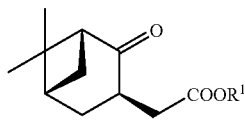

(II)

wherein R$^1$ is alkyl, which comprises reacting a compound (I):

(I)

with XCH$_2$COOR$^1$ wherein X is halogen, and R$^1$ is as defined above in the presence of an additive selected from the group consisting of N,N'-dimethylpropyleneurea and 1,3-dimethyl-2-imidazolidinone and a base.

2. A process for the preparation of a compound (X):

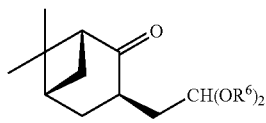

(X)

wherein R$^6$ each is independently alkyl, which comprises reacting a compound (IX):

(IX)

wherein R$^5$ each is independently alkyl, with CH$_2$=CHOR$^6$ wherein R$^6$ is as defined above in the presence of ceric ammonium nitrate (IV) in a solvate of R$^6$OH wherein R$^6$ is as defined above.

3. A process for the preparation of a compound (X):

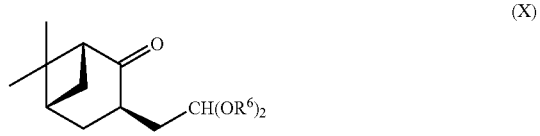

(X)

wherein each R$^6$ is independently alkyl, which comprises preparing a compound (IX):

(IX)

wherein each R$^5$ is independently alkyl, by reacting a compound (I):

(I)

with (R$^5$)$_3$SiX wherein R$^5$ is as defined above, and X is halogen, in the presence of a base, and reacting the compound (IX) with CH$_2$=CHOR$^6$ wherein R$^6$ is as defined above in the presence of ceric ammonium nitrate (IV) in a solvent of R$^6$OH wherein R$^6$ is as defined above.

* * * * *